United States Patent [19]

McClelland

[11] Patent Number: 5,790,617
[45] Date of Patent: Aug. 4, 1998

[54] METHOD AND APPARATUS FOR DETECTION OF FAILED FUEL RODS BY USE OF ACOUSTIC ENERGY FREQUENCY ATTENUATION

[75] Inventor: Richard G. McClelland, Richland, Wash.

[73] Assignee: Siemens Power Corporation, Richland, Wash.

[21] Appl. No.: 563,860

[22] Filed: Nov. 29, 1995

Related U.S. Application Data

[63] Continuation-in-part of Ser. No. 422,015, Apr. 12, 1995, abandoned, which is a continuation of Ser. No. 48,562, Apr. 14, 1993, abandoned, which is a continuation of Ser. No. 858,265, Mar. 26, 1992, abandoned.

[51] Int. Cl.$^6$ .................. G21C 17/00; G21C 17/06; G01N 29/14
[52] U.S. Cl. .................. 376/252; 376/245; 376/250; 376/251; 73/577; 73/622; 73/624
[58] Field of Search ............... 376/250, 251, 376/252, 245; 73/622, 624, 577

[56] References Cited

U.S. PATENT DOCUMENTS

| | | | |
|---|---|---|---|
| 3,063,290 | 11/1962 | Kaserman et al. | 73/67.8 |
| 3,350,271 | 10/1967 | Maidment et al. | 176/19 |
| 3,552,190 | 1/1971 | Lefebvre | 73/67.7 |
| 3,855,847 | 12/1974 | Leschek | 73/71.4 |
| 4,009,616 | 3/1977 | Wonn | 73/398 R |
| 4,052,889 | 10/1977 | Mucciardi et al. | 73/67.85 |
| 4,126,514 | 11/1978 | Wonn | 176/19 LD |
| 4,174,255 | 11/1979 | Lawrie | 176/19 LD |
| 4,193,843 | 3/1980 | Womack et al. | 176/19 LD |
| 4,228,804 | 10/1980 | Holasek et al. | 128/660 |
| 4,265,122 | 5/1981 | Cook et al. | 73/627 |
| 4,366,711 | 1/1983 | Weilbacher et al. | 73/590 |
| 4,410,484 | 10/1983 | Marini et al. | 376/252 |
| 4,428,236 | 1/1984 | Votava et al. | 73/587 |
| 4,443,402 | 4/1984 | Marini et al. | 376/252 |
| 4,517,152 | 5/1985 | Pieper et al. | 376/252 |
| 4,605,531 | 8/1986 | Leseur et al. | 376/252 |
| 4,613,978 | 9/1986 | Kurth et al. | 375/99 |
| 4,681,730 | 7/1987 | Beuneche et al. | 376/252 |
| 4,684,493 | 8/1987 | Gravelle | 376/252 |
| 4,866,614 | 9/1989 | Tam | 364/413.25 |
| 4,879,088 | 11/1989 | Van Swam et al. | 376/252 |
| 5,118,463 | 6/1992 | Bordy et al. | 376/252 |
| 5,343,760 | 9/1994 | Sultan et al. | 73/861.04 |

FOREIGN PATENT DOCUMENTS

| | | |
|---|---|---|
| 0 018 290 | 10/1980 | European Pat. Off. |
| 0 082 102 | 3/1984 | European Pat. Off. |
| 0 115 231 | 8/1984 | European Pat. Off. |
| 0 178 860 | 4/1986 | European Pat. Off. |
| 0 229 837 | 7/1987 | European Pat. Off. |

*Primary Examiner*—Kathryn L. Gorgos
*Assistant Examiner*—Chrisman D. Carroll
*Attorney, Agent, or Firm*—Ira Lee Zebrak

[57] ABSTRACT

A system and method of the present invention measures the relative stress in the cladding of a nuclear fuel rod caused by the internal gas pressure of the rod. This is done by determining the attenuation ratio of two specific frequencies from a broadband low frequency acoustic energy spectrum. Relative pressure differentials are measurable and therefore any loss of fuel rod gas pressure is a direct indication of fuel rod cladding failure.

20 Claims, 3 Drawing Sheets

METHOD AND APPARATUS FOR DETECTION OF FAILED FUEL RODS BY USE OF ACOUSTIC ENERGY FREQUENCY ATTENUATION

CROSS-REFERENCE TO RELATED APPLICATIONS

This is a continuation-in-part application of U.S. application Ser. No. 08/422,015 filed Apr. 12, 1995, now abandoned, which is a continuation of U.S. application Ser. No. 08/048,562, filed Apr. 14, 1993, now abandoned, which is a continuation of U.S. application Ser. No. 07/858,265, filed Mar. 26, 1992, now abandoned.

BACKGROUND OF THE INVENTION a) Field of the Invention

The present invention relates to a system and method for detecting failed fuel rods and, in particular, it relates to a system and method for providing a relative measure of internal fuel rod pressure by measuring the frequency dependent attenuation of an acoustic energy spectrum so that a failed fuel rod may be detected.

b) Background Art

Detection of defects in nuclear fuel rods is normally performed by either ultrasonic testing or sipping. In ultrasonic testing, water in the fuel rods (indicating failure) is detected by measuring the difference in attenuation of the ultrasonic energy returned from a water (failed rod) or gas (sound rod) interface of the cladding interior wall. An example of this approach is set forth in U.S. Pat. No. 4,879,088, assigned to the same assignee as that of the present invention. In sipping, wet or dry, the method detects fission gases being released from a failed rod. In either case, conditions exist, such as pellet clad interaction or extremely small leaks, that limit the effectiveness of both methods.

U.S. Pat. No. 4,126,514 discloses a method for detecting defective fuel elements by isolating from contact the exterior surface of a fuel element cladding from the cooling liquid normally employed and then making a pulsed echo attenuation measurement to identify the presence of excessively swollen fuel pellets. The measure of the presence of either cooling liquid within the element or a number of swollen fuel pellets is achieved by appropriate interpretation of echo pulses.

U.S. Pat. No. 3,350,271 discloses a nuclear reactor transducer which contains a liquid therein such that heat transfer to the transducer heats the liquid. Under normal operating conditions, the pressure keeps the liquid as a liquid. Boiling of the liquid in the transducer, detected ultrasonically, could be used as an indication of the attainment of a predetermined pressure. Should there be a leak in the fuel rod, there would be a drop in pressure and, thus, the liquid would vaporize and expand through an orifice to indicate that a leak has occurred.

Neither U.S. patent mentioned immediately above measures stress by ultrasonic means to determine the internal pressure of a fuel rod as will be described below in accordance with the present invention.

U.S. Pat. No. 4,009,616 is directed to an acoustic method for measuring gas pressure in a hermetically sealed enclosure. This is done by determining the velocity change and attenuation of an ultrasonic signal caused by the internal gas pressure within the enclosure (fuel rod). This process requires that the signal be transmitted through the gas and the effects of the signal received through the cladding be minimized. This differs from the below described apparatus and method of the present invention which measures the relative stress in the fuel cladding material which is a resultant of the internal gas pressure. Additionally, the process of U.S. Pat. No. 4,009,616 is impractical for actual use since virtually all fuel rods have plenum springs in the area mentioned which would either totally block or destroy all necessary information contained in the acoustic data (i.e. velocity and attenuation).

A further limitation of prior art methods is that., in most cases, fuel rod failure tests cannot be made in an actual working reactor core.

SUMMARY OF THE INVENTION

It is an object of the present invention to overcome the difficulties of the prior art fuel rod failure detection methods and to provide a more reliable and repeatable rod failure detection method and system. A further object is to provide a system for rod failure detection in a reactor environment (i.e., "in situ").

In accordance with the present invention, a system for the detection of failed nuclear fuel rods comprises transmitter means for providing a source of electrical energy and first transducer means responsive to the transmitter means for applying pulsed ultrasonic energy of a specified frequency directly to external cladding of a nuclear fuel rod. Second transducer means, spaced apart from the first transducer means, receives ultrasonic energy transmitted through and along the fuel rod and provides an electrical signal in response thereto. The second transducer means are positioned adjacent the external cladding of the nuclear fuel rod. Receiving means are included, which are responsive to the signal from the second transducer, for processing high and low frequency components of said signal and for providing an output signal. A gated multi-channel spectrum analyzer is responsive to the output signal of the receiving means for determining the spectral component of the received ultrasonic energy over a lower and a higher frequency range and for producing resultant signals proportional to the amplitude of each frequency component. The resultant signals are a measure of stress of the cladding and consequent pressure differentials so that any loss of fuel rod gas pressure will be a direct measure of fuel cladding failure.

For a better understanding of the present invention, reference is made to the following description and accompanying drawings while the scope of the invention will be pointed out in the appended claims.

DESCRIPTION OF THE PREFERRED EMBODIMENTS

The system and method of the present invention generally measures the relative stress in the cladding of a nuclear fuel rod caused by the internal gas pressure in the rod. This is done by determining the attenuation ratio of two specific frequencies from a broadband low frequency acoustic energy spectrum. Relative pressure differentials are measurable and therefore any loss of fuel rod gas pressure is a direct indication of fuel rod cladding failure.

Figure 1:
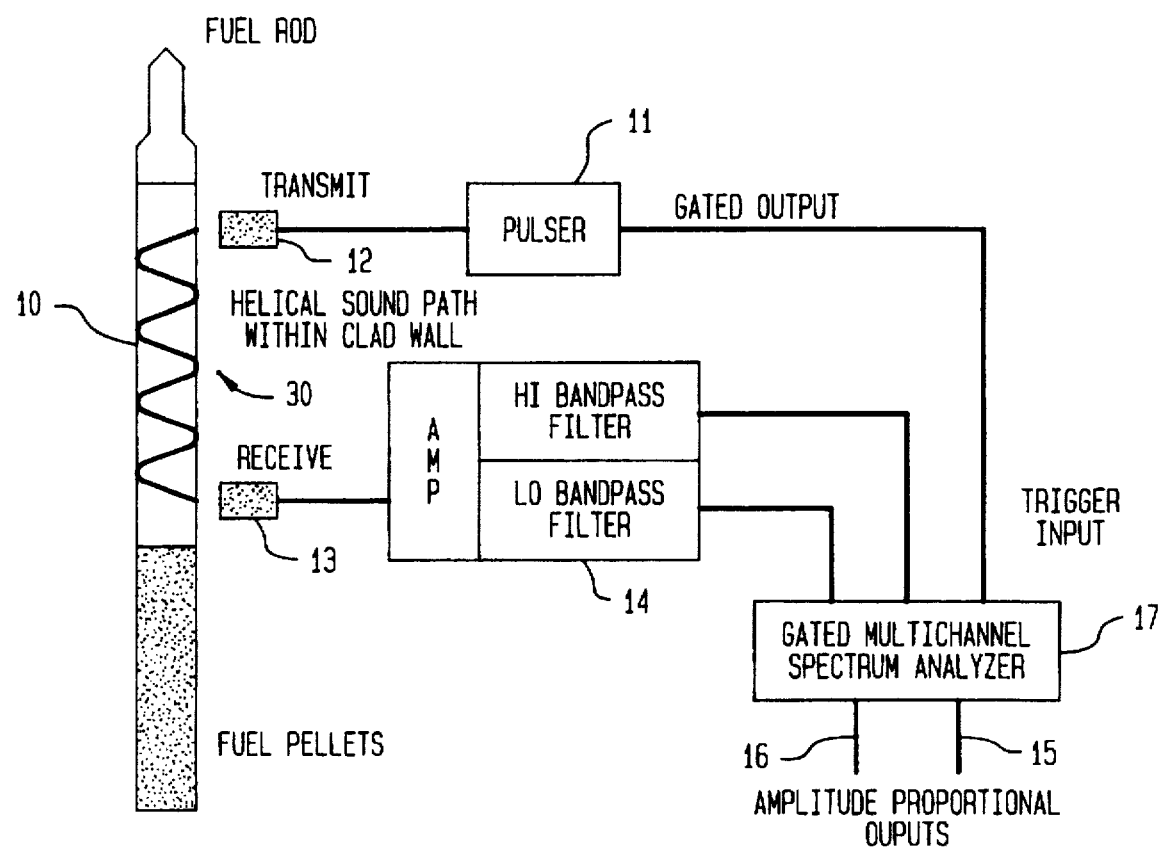
FIG. 1 represents a simplified block diagram of the apparatus of the present invention.

Referring to FIG. 1. the system of the present invention is shown. A fuel rod 10 is under test by applying broadband pulsed ultrasonic energy to the fuel rod. This is accomplished by supplying electrical energy from a transmitter 11 to first acoustic transducer 12. The transmitter is preferably in the form of piezoelectric crystal which operates at a resonant frequency of 300 Khz. A second acoustic transducer 13, spaced apart from the first acoustic transducer, functions as a receiving element. Both transducers are aligned on the plenum region 30 as to produce a multi turn helical acoustic path around the fuel rod plenum region. The transducers are not normally in direct contact with the fuel rods. To minimize near field effect of the transducers, a gap of 0.050 inch is maintained.. This distance, however, is not critical. Acoustic transducer 13 supplies its energy to a receiver 14 comprising an amplifier section and high and low bandpass filters. The filter outputs are then supplied to a gated multi-channel spectrum analyzer 17 with appropriate band-pass filters. The spectrum analyzer 17 is gated by a signal from the transmitter 11.

The transmitter is pulsed at a predetermined rate and the frequency spectrum of the energy conveyed through the cladding is received by the receiving crystal of the second transducer which in turn is supplied through receiver 14 to the spectrum analyzer 17. The spectrum analyzer 17 filters the two frequency bands of interest and produces signals 15, 16 proportional to the amplitude of each frequency component. The attenuation of the lower frequencies, ≈100 Khz, is more pronounced than the higher frequencies due to stress factors in the cladding. The amount of attenuation of the lower frequencies directly relates to the stresses (or internal gas pressure), of the cladding. The above description applies whether the rods are measured in a reactor core or in a spent fuel pool ("in situ") or if they are measured outside of such environment.

Specific tests were run by the inventor to determine whether the presence or absence of 500 psi gas (the maximum expected at the end of life of a PWR fuel rod; during fuel cycles the pressure in the sound fuel rods an only increase due to fission gas release from the pellets) inside Zircaloy 4 inert fuel rods. Five rods, all having internal springs, one having zero pressure, one having 60 psi pressure, one having 390 psi pressure and two having high unspecified pressures, constituted the experimental samples. PWR rods are typically filled with ≈390 psi. BWR rods are typically filled with ≈60 psi. The tests were run in a water bath. It should be understood that measurements do not have to be made underwater as long as there is an acceptable coupling medium to pass the acoustic signal. For application to irradiated nuclear fuel, all testing must be done underwater to reduce the very high radiation exposure to personnel.

If a fuel rod fails, it is expected that the majority of the gas will escape and the remaining will equalize with external water pressure (≈15 psi outside the reactor core where testing would occur).

In the tests a broadband pulse was launched by the transmitter with most of its energy in the 50 Khz to 1 Mhz range. The pulse was detected with two channels having different bandpass filters preferably 100–300 Khz and 600–1200 Khz. Transducer spacing of about six inches apart was preferable. It is also preferable that the transducer spacing cover as much of the plenum area as possible (typically six inches to 11 inches). The transducers had a center frequency of 300 Khz. The received signal was digitized and used to calculate a frequency spectrum using the Fast Fourier Transform (FFT).

Figure 2:
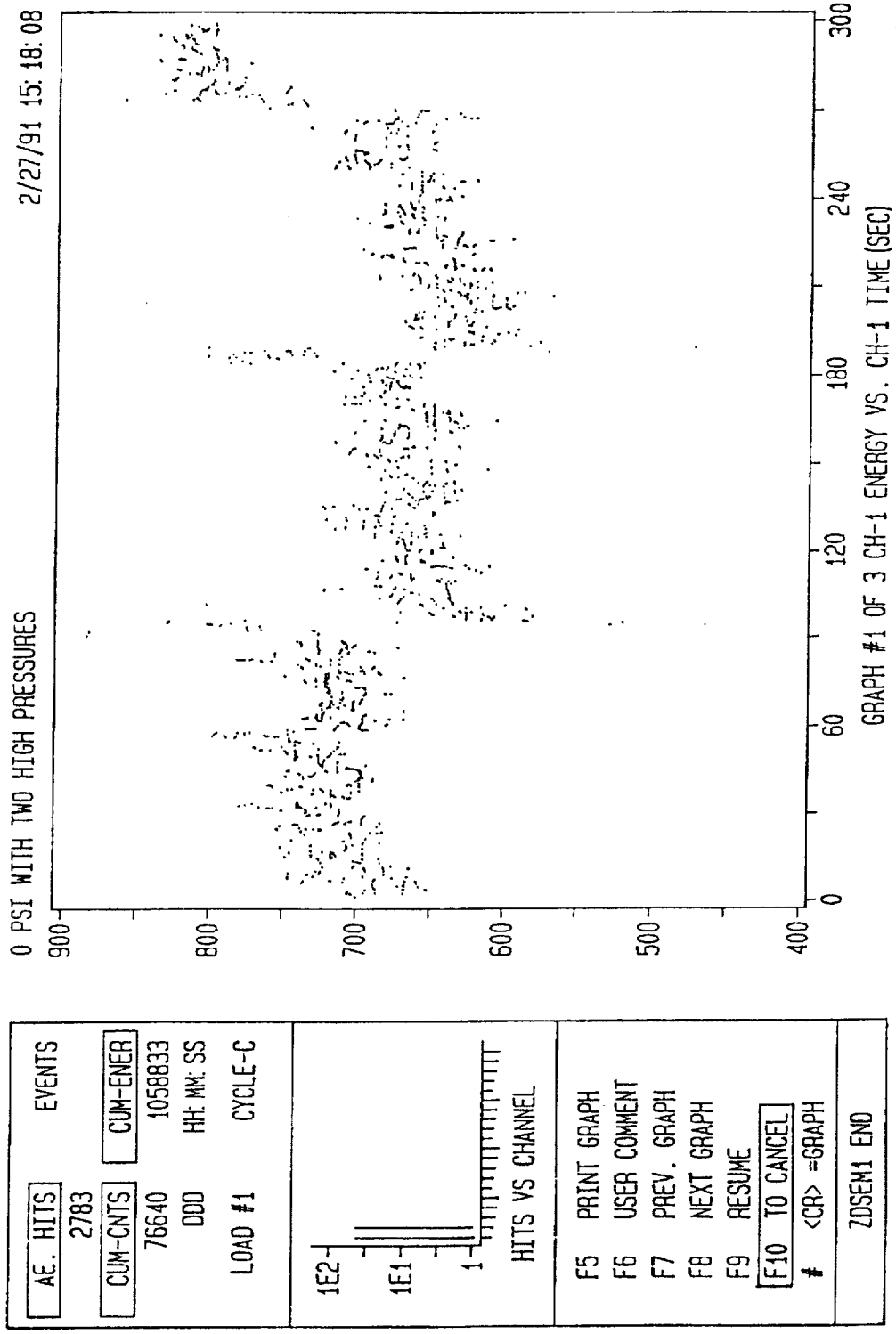
FIGS. 2 and 3 illustrate actual data obtained from a low pressure and two high pressure fuel rods.

Referring to FIG. 2, a frequency spectrum display of 100–300 Khz is depicted based on measurements of a 0 psi rod and two 390 psi pressure rods indicates desired, repeatable correlation with internal fuel rod pressure. The left set of scatter data points represent 0 psi while the right sets are from two different 390 psi rods. The vertical (y offset) of the mean of the scatter plots represents the difference in attenuation factors.

Figure 3:
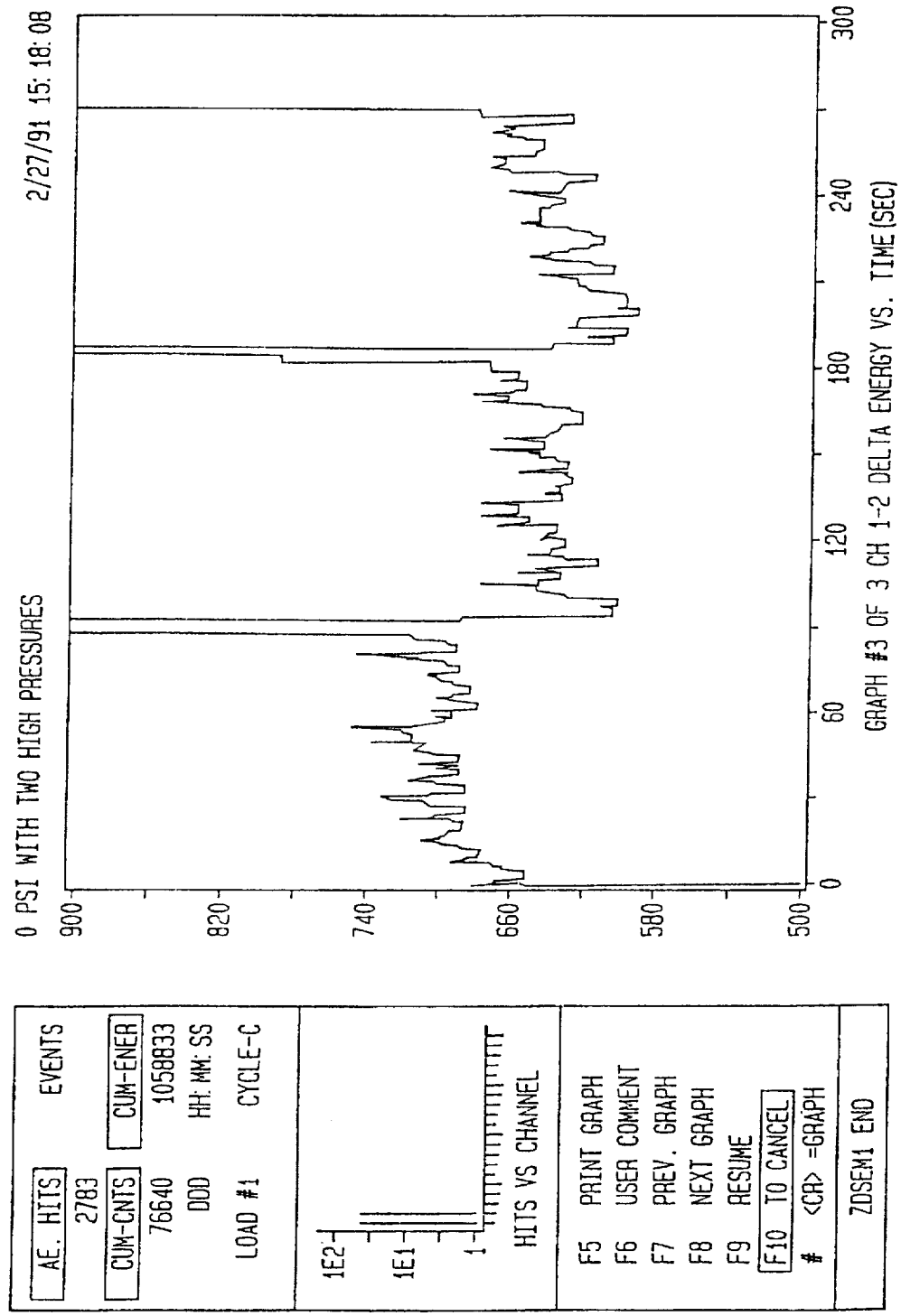

In FIG. 3, the difference between 100 Khz–300 Khz and 600–1200 Khz energy values for the same three rods is shown which indicates the desired correlation with less scatter (0 psi on the left). In both FIGS. 2 and 3, the 0 psi condition is clearly distinguishable from high pressure conditions.

The measurement process is based on the ability to measure small variations in the acoustic velocity and attenuation of Plate –versus–Longitudinal waves. These variations, it is believed, are proportional to the cladding stress and cause wave interactions at the receiving transducer. The frequencies determined during the test which gave best attenuation ratios were 100–300 Khz v. 600–1200 Khz although the present invention is not specifically limited to these ranges. As understood, the system of the invention is not intended to provide a measurement standard but rather to determine individual rod failures based on the signal amplitude population distribution of individual fuel assemblies.

This would normalize perturbations caused by variable fission gas release (slight pressure differentials between individual rods).

It is an important aspect of the present invention that the failure rod detection method and apparatus allows use in either a reactor environment, that is, when the fuel rods are in a reactor core or in a spent fuel pool: ("in situ") or outside of a reactor environment.

While the foregoing description and drawings represent the preferred embodiments of the present invention, it will be obvious to those skilled in the art that various changes and modifications may be made therein without departing from the true spirit and scope of the present invention.

What is claimed is:

1. A system for the detection of failed nuclear fuel rods in situ comprises:

transmitter means for providing a source of pulsed electrical energy;

first transducer means responsive to said transmitter means for applying pulsed ultrasonic energy of a specified frequency bond directly to external cladding of a nuclear fuel rod;

second transducer means, spaced apart from said first transducer means, for receiving ultrasonic energy transmitted through and along said fuel rod and for providing an electrical signal in response thereto, said second transducer means being positioned adjacent the external cladding of said nuclear fuel rod; said first and second transducer means being positioned adjacent the plenum region of the fuel rod;

receiving means responsive to said signal from said second transducer, for processing frequency components of two different frequency ranges of said signal and for providing an output signal; and a gated multi-channel spectrum analyzer, responsive to said output signal from said receiving means, for determining the spectral component of the received ultrasonic energy over a first and a second frequency range and for producing resultant signals proportional to the amplitude of each frequency component, said resultant signals being a measure of the stress of the cladding and consequent pressure differentials so that any loss of fuel rod gas pressure will be a direct measure of fuel cladding failure.

2. The system of claim 1 wherein the transmitter means provide pulsed signals at a frequency of approximately 300 Khz.

3. The system of claim 1 wherein said second transducer means is a wide band receiver.

4. The system of claim 1 wherein said spectrum analyzer analyzes signals in a first frequency range of about 100–300 Khz and signals in a second frequency range of about 600–1200 KHZ.

5. The system of claim 1 wherein said first transducer means applies broadband pulses in the 50 Khz to 1 Mhz range.

6. The system of claim 1 wherein said fuel rods are immersed in a water bath.

7. The system of claim 1 wherein said resultant signals represent an attenuation change of the first range of frequencies, said first range of frequencies being lower than said second range.

8. The system of claim 1 wherein said receiving means includes an amplifier portion and bandpass filters covering a first and second frequency range..

9. A method for detection of failed nuclear rods in situ comprises:

applying broadband pulses of ultrasonic energy to the plenum area of a nuclear fuel rod;

sensing, in response to said applied ultrasonic energy, the measured ultrasonic response of said rod in said plenum area;

converting such measured response to an electrical signal;

determining by spectral analysis the spectral component of said electrical signal over a first and a second frequency range and producing resultant signals proportional to the amplitude of each frequency component;

wherein said resultant signals are a measure of the stress of the cladding of the rod and consequent pressure differential so that any loss of fuel rod gas pressure will be a direct measure of fuel cladding failure.

10. The method of claim 9, further comprising the step of generating a signal encoding the difference between the amplitude of each frequency component.

11. A system for the detection of failed nuclear fuel rods comprises:

transmitter means for providing a source of pulsed electrical energy;

first transducer means responsive to said transmitter means for applying pulsed ultrasonic energy of a specified frequency bond directly to external cladding of a nuclear fuel rod;

second transducer means, spaced apart from said first transducer means, for receiving ultrasonic energy transmitted through and along said fuel rod and for providing an electrical signal in response thereto, said second transducer means being positioned adjacent the external cladding of said nuclear fuel rod;

receiving means responsive to said signal from said second transducer, for processing frequency components of two different frequency ranges of said signal and for providing an output signal; and a gated multi-channel spectrum analyzer, responsive to said output signal from said receiving means, for determining the spectral component of the received ultrasonic energy over a first and a second frequency range and for producing resultant signals proportional to the amplitude of each frequency component, said resultant signals being a measure of the stress of the cladding and consequent pressure differentials so that any loss of fuel rod gas pressure will be a direct measure of fuel cladding failure.

12. The system of claim 11 wherein the transmitter means provide pulsed signals at a frequency of approximately 300 Khz.

13. The system of claim 11 wherein said second transducer means is a wide band receiver.

14. The system of claim 11 wherein said spectrum analyzer analyzes signals in a first frequency range of about 100–300 Khz and signals in a second frequency range of about 600–1200 KHZ.

15. The system of claim 11 wherein said first transducer means applies broadband pulses in the 50 Khz to 1 Mhz range.

16. The system of claim 11 wherein said fuel rods are immersed in a water bath.

17. The system of claim 11 wherein said resultant signals represent an attenuation change of the first range of frequencies, said first range of frequencies being lower than said second range.

18. The system of claim 11 wherein said receiving means includes an amplifier portion and bandpass filters covering a first and second frequency range.

19. A method for detection of failed nuclear rods comprises:

applying broadband pulses of ultrasonic energy to a nuclear fuel rod;

sensing, in response to said applied ultrasonic energy, the measured ultrasonic response of said rod;

converting such measured response to an electrical signal;

determining by spectral analysis the spectral component of said electrical signal over a first and a second frequency range and producing resultant signals proportional to the amplitude of each frequency component;

wherein said resultant signals are a measure of the stress of the cladding of the rod and consequent pressure differential so that any loss of fuel rod gas pressure will be a direct measure of fuel cladding failure.

20. The method of claim 19, further comprising the step of generating a signal encoding the difference between the amplitude of each frequency component.

\* \* \* \* \*